United States Patent [19]

Maruyama et al.

[11] Patent Number: 5,238,921
[45] Date of Patent: Aug. 24, 1993

[54] OLIGOPEPTIDE, ANGIOTENSIN CONVERTING ENZYME INHIBITORS, HYPOTENSIVE AGENT, AND METHOD FOR TREATMENT OF HYPERTENSION

[75] Inventors: Susumu Maruyama; Hideoki Tanaka; Hidekatsu Maeda, all of Tsukuba; Shinsuke Miyoshi; Hiromi Ishikawa, both of Funabashi; Fumio Fukui, Narita, all of Japan

[73] Assignees: Agency of Industrial Science and Technology; Showa Sangyo Co., Ltd., Tokyo, Japan

[21] Appl. No.: 660,878

[22] Filed: Feb. 26, 1991

[30] Foreign Application Priority Data

Feb. 27, 1990 [JP] Japan .................................. 2-44388
Mar. 30, 1990 [JP] Japan .................................. 2-80885

[51] Int. Cl.$^5$ ...................... A61K 37/02; C07K 5/06; C07K 5/08; C07K 7/06
[52] U.S. Cl. ........................... 514/18; 514/17; 530/329; 530/330; 530/331
[58] Field of Search .................. 530/329, 330, 331; 514/17-18

[56] References Cited

U.S. PATENT DOCUMENTS

| | | | |
|---|---|---|---|
| Re. 29,732 | 8/1978 | Flouret ................................ | 530/331 |
| 4,305,872 | 12/1981 | Johnston et al. .................... | 530/331 |
| 4,780,528 | 10/1988 | Takemoto et al. ................... | 530/331 |
| 4,900,658 | 2/1990 | Konig et al. ........................ | 530/331 |
| 5,008,246 | 4/1991 | Schon et al. ........................ | 514/18 |
| 5,041,535 | 8/1991 | Nyeki et al. ......................... | 514/18 |

FOREIGN PATENT DOCUMENTS

| | | | |
|---|---|---|---|
| 0099286 | 1/1984 | European Pat. Off. ............. | 514/18 |
| 0316218 | 5/1989 | European Pat. Off. ............. | 514/18 |

*Primary Examiner*—Lester L. Lee
*Attorney, Agent, or Firm*—Antonelli, Terry, Stout & Kraus

[57] ABSTRACT

L-Tyr-L-Val, L-Leu-L-Tyr, L-Leu-L-Pro, L-Phe-L-Tyr, L-Tyr-L-Arg and its acid addition salts, L-Leu-L-Ser-L-Pro, L-Leu-L-Gln-L-Pro, L-Phe-L-Leu-L-Pro, L-Leu-L-Leu-L-Pro, L-Leu-L-Asn-L-Pro, L-Phe-L-Pro, L-Leu-L-Ala-L-Ala, L-Val-L-Ala-L-Ala, L-Leu-L-Gln-L-Gln, L-Val-L-Ala-L-Tyr, L-Leu-L-Ala-L-Tyr, L-Leu-L-Ser-L-His and its acid solution salts, L-Ile-L-Arg-L-Ala and its acid addition salts, L-Leu-L-Arg-L-Pro and its acid addition salts, and L-Ile-L-Arg-L-Ala-L-Gln-L-Gln and its acid addition salts, derived from a corn protein α-zein, and tripeptides represented by the formula $$\text{L-(or D-) Leu-L-}X_{aa}\text{-L-Pro}$$

wherein $X_{aa}$ is Gly, Ala, Val, Ile, Thr, Asp, Glu, Lys, Orn, Cys, Met, Phe, Tyr, Trp, His or a hydroxyproline residue, pharmacologically acceptable acid addition salts of the above tripeptides wherein $X_{aa}$ is Lys, Orn, His or Arg, and pharmacologically acceptable alkali or alkaline earth metal salts, ammonium salts or organic base salts of the tripeptides wherein $X_{aa}$ is Asp or Glu, have an angiotensin converting enzyme-inhibiting activity.

26 Claims, No Drawings

OLIGOPEPTIDE, ANGIOTENSIN CONVERTING ENZYME INHIBITORS, HYPOTENSIVE AGENT, AND METHOD FOR TREATMENT OF HYPERTENSION

BACKGROUND OF THE INVENTION

This invention relates to novel oligopeptides either derived from a corn protein or synthesized, an angiotensin converting enzyme inhibitor containing as an effective ingredient at least one of the oligopeptides, a hypotensive agent containing as an effective ingredient at least one of the oligopeptides, a method for inhibition of the angiotensin converting enzyme using at least one of certain oligopeptides, and a method for treatment or prophylaxis of hypertension using at least one of certain oligopeptides.

It is well known that the renin-angiotensin system has profound relation to crisis of hypertension, and in this renin-angiotensin system the angiotensin converting enzyme (EC 3.4.15.1, hereinafter sometimes referred to as ACE) plays an important role. Namely, ACE acts on angiotensin I (Asp-Arg-Val-Tyr-Ile-His-Pro-Phe-His-Leu) formed by decomposition of angiotensin, which was secreted in the liver, by an enzyme renin produced in the kidney, and converts it to angiotensin II (Asp-Arg-Val-Tyr-Ile-His-Pro-Phe). This angiotensin II has activities, for example, to heighten the blood pressure by contracting the smooth muscles of the blood vessel walls and further promote secretion of aldosterone by action on the adrenal cortex. Separately, an enzyme kallikrein, which exists in the plasma, decomposes a protein called kininogen to produce bradykinin which dilates the blood vessel and lowers the blood pressure, but this bradykinin is decomposed and inactivated by action of ACE. Thus, ACE forms, on the one hand, a blood pressure heightening peptide (angiotensin II), and decomposes, on the other hand, a blood pressure lowering peptide (bradykinin), and as a result heighten the blood pressure. Therefore, it is possible to prevent increase of the blood pressure (lowering of the blood pressure) by inhibition of activities of this enzyme.

Heretofore, there have been known many ACE activity inhibiting substances, for example, several peptidic inhibitors, as the starter, obtained from snake venoms, and synthetic substances such as captopril (D-2-methyl-3-mercaptopropanoyl-L-proline). Among them captopril is already practically used as an oral hypotensive agent.

Further, recently, ACE inhibiting substances were found also in microorganisms and various foods and are being investigated for putting them to practical use as a hypotensive agent (Kunio Suetsuna, "Hakko to Kogyo" (Fermentation and Industry) 46 (No. 3), 179–182 (1988)). Further, a report on ACE inhibiting substances derived from food proteins, particularly, casein and corn seed proteins was made in Susumu Maruyama, Biosciences and Industry 47 (No. 11), 38-42 (1989). Further, reports were also made on ACE inhibiting substances derived from corn seed proteins in Susumu Maruyama et al., Lecture Gists for the 1988 Year Great Annual Meeting of Nippon Hakko Kogaku Kai (Japan Fermentation Engineering Society), p. 23 (1988); Susumu Maruyama et al., Lecture Gists for the 1989 Year Meeting of Nippon Nogei Kagaku Kai (Japan Society for Bioscience, Biotechnology and Agrochemistry), p. 8 (1989); Shinsuke Miyoshi et al., Gists for the 1989 Year Meeting of Nippon Eiyo Shokuryo Gakki (Japan Nutrition and Food Society) p. 113 (1989); and Shinsuke Miyoshi et al., Nippon Nogei Kagaku Kaishi (Journal of Japan Agricultural Chemistry Society), 64(3), 555, 1990 (Lecture Gists for the 1990 Year Great Annual Meeting).

SUMMARY OF THE INVENTION

Novel and useful hypotensive agents and angiotensin converting enzyme inhibitors are always sought, and bring about abundance of the techniques.

The object of the invention is to provide novel oligopeptides having an excellent angiotensin converting enzyme-inhibiting activity; an angiotensin converting enzyme inhibitor containing such an oligopeptide as an effective ingredient and having extremely high safety; a hypotensive agent containing as an effective ingredient such an oligopeptide and having extremely high safety; a method for inhibition of the angiotensin converting enzyme using a certain oligopeptide; and a method for treatment or prophylaxis of hypertension using a cetain oligopeptide.

The above objects have been attained by the following inventions having relation to certain oligopeptides either derived from α-zein, a corn protein, or synthesized:

1. L-Leu-L-Ser-L-Pro, L-Leu-L-Gln-L-Pro, L-Val-L-Ser-L-Pro L-Leu-L-Leu-L-Pro, L-Leu-L-Asn-L-Pro, L-Phe-L-Leu-L-Pro, L-Leu-L-Ala-L-Ala, L-Val-L-Ala-L-Ala, L-Leu-L-Gln-L-Gln, L-Val-L-Ala-L-Tyr, L-Leu-L-Ala-L-Tyr, L-Leu-L-Ser-L-His and its acid addition salts, L-Ile-L-Arg-L-Ala and its acid addition salts, L-Leu-L-Arg-L-Pro and its acid addition salts, and L-Ile-L-Arg-L-Ala-L-Gln-L-Gln and its acid addition salts, and tripeptides represented by the formula

wherein $X_{aa}$ is Gly, Ala, Val, Ile, Thr, Asp, Glu, Lys, Orn, Cys, Met, Phe, Tyr, Trp, His or a hydroxyproline residue, and acid addition salts of the above tripeptides wherein $X_{aa}$ is Lys, Orn, His or Arg, and alkali or alkaline earth metal salts, ammonium salts or organic base salts of the above tripeptides wherein $X_{aa}$ is Asp or Glu.

2. An angiotensin converting enzyme inhibitor which either comprises at least one member which is selected from the group consisting of L-Leu-L-Ser-L-Pro, L-Leu-L-Gln-L-Pro, L-Val-L-Ser-L-pro, L-Leu-L-Leu-L-Pro, L-Leu-L-Asn-L-Pro, L-Phe-L-Leu-L-Pro, L-Leu-L-Ala-L-Ala, L-Val-L-Ala-L-Ala, L-Leu-L-Gln-L-Gln, L-Val-L-Ala-L-Tyr, L-Leu-L-Ala-L-Tyr, L-Leu-L-Ser-L-His or its pharmacologically acceptable acid addition salt, L-Ile-L-Arg-L-Ala or its pharmacologically acceptable acid addition salt, L-Leu-L-Arg-L-Pro or its pharmacologically acceptable acid addition salt, L-Ile-L-Arg-L-Ala-L-Gln-L-Gln or its pharmacologically acceptable acid addition salt, and a tripeptide represented by the formula

wherein $X_{aa}$ is Gly, Ala, Val, Ile, Thr, Asp, Glu, Lys, Orn, Cys, Met, Phe, Tyr, Trp, His or a hydroxyproline residue or a pharmacologically acceptable acid addition salt of the above tripeptide wherein $X_{aa}$ is Lys, Orn, His or Arg, or a pharmacologically acceptable alkali or alkaline earth metal salt, ammonium salt or organic base salt of the tripeptide wherein $X_{aa}$ is Asp or Glu, and is in an amount effective to inhibit the angiotensin converting enzyme of a human being or another mammal, and, if needed, pharmacologically acceptable carrier (s); or is in the from of food containing said at least one member in the same amount as above.

3. A hypotensive agent for human being or another mammal which either comprises a hypotensively effective amount of at least one member selected from the group consisting of L-Leu-L-Ser-L-Pro, L-Leu-L-Gln-L-Pro, L-Val-L-Ser-L-Pro, L-Leu-L-Leu-L-Pro, L-Leu-L-Asn-L-Pro, L-Phe-L-Leu-L-Pro, L-Leu-L-Ala-L-Ala, L-Val-L-Ala-L-Ala, L-Leu-L-Gln-L-Gln, L-Val-L-Ala-L-Tyr, L-Leu-L-Ala-L-Tyr, L-Leu-L-Ser-L-His or its pharmacologically acceptable acid addition salt, L-Ile-L-Arg-L-Ala or its pharmacologically acceptable acid addition salt, L-Leu-L-Arg-L-Pro or its pharmacologically acceptable acid addition salt, and L-Ile-L-Arg-L-Ala-L-Gln-L-Gln or its pharmacologically acceptable acid addition salt, and a tripeptide represented by the formula L-(or D-) Leu-L-X$_{aa}$-L-Pro wherein X$_{aa}$ is Gly, Ala, Val, Ile, Thr, Asp, Glu, Lys, Orn, Cys, Met, Phe, Tyr, Trp, His or a hydroxyproline residue or a pharmacologically acceptable acid addition salt of the above tripeptide wherein X$_{aa}$ is Lys, Orn, His or Arg, or a pharmacologically acceptable alkali or alkaline earth metal salt, ammonium salt or organic base salt of the tripeptide wherein X$_{aa}$ is Asp or Glu, and if needed, pharmaceutically acceptable carrier(s); or is in the form of a food containing a hypotensively effective amount of said at least one member.

4. A method for inhibition of the angiotensin converting enzyme in the body of a human being or another mammal which comprises administering to the human being or another mammal at least one member which is selected from the group consisting of L-Tyr-L-Val, L-Leu-L-Tyr, L-Leu-L-Phe, L-Phe-L-Tyr, L-Tyr-L-Arg or its pharmacologically acceptable acid addition salt, L-Leu-L-Ser-L-Pro, L-Leu-L-Gln-L-Pro, L-Val-L-Ser-L-Pro, L-Leu-L-Leu-L-Pro, L-Leu-L-Asn-L-Pro, L-Phe-L-Leu-L-Pro, L-Leu-L-Ala-L-Ala, L-Val-L-Ala-L-Ala, L-Leu-L-Gln-L-Gln, L-Val-L-Ala-L-Tyr, L-Leu-L-Ala-L-Tyr, L-Leu-L-Ser-L-His or its pharmacologically acceptable acid addition salt, L-Ile-L-Arg-L-Ala or its pharmacologically acceptable acid addition salt, L-Leu-L-Arg-L-Pro or its pharmacologically acceptable acid addition salt, and L-Ile-L-Arg-L-Ala-L-Gln-L-Gln or its pharmacologically acceptable acid addition salt, and a tripeptide represented by the formula L-(or D-) Leu-L-X$_{aa}$-L-Pro wherein X$_{aa}$ is Gly, Ala, Val, Ile, Thr, Asp, Glu, Lys, Orn, Cys, Met, Phe, Tyr, Trp, His or a hydroxyproline residue or a pharmacologically acceptable acid addition salt of the above tripeptide wherein X$_{aa}$ is Lys, Orn, His or Arg, or a pharmacologically acceptable alkali or alkaline earth metal salt, ammonium salt or organic base salt of the tripeptide wherein X$_{aa}$ is Asp or Glu, and is in an amount effective to inhibit the angiotensin converting enzyme.

5. A method for treatment or prophylaxis of hypertension of a human being or another mammal which comprises administering to the human being or another mammal a hypotensively effective amount of at least one member selected from the group consisting of L-Tyr-L-Val, L-Leu-L-Tyr, L-Leu-L-Phe, L-Phe-L-Tyr, L-Tyr-L-Arg or its pharmacologically acceptable acid addition salt, L-Leu-L-Ser-L-Pro, L-Leu-L-Gln-L-Pro, L-Val-L-Ser-L-Pro, L-Leu-L-Leu-L-Pro, L-Leu-L-Asn-L-Pro, L-Phe-L-Leu-L-Pro, L-Leu-L-Ala-L-Ala, L-Val-L-Ala-L-Ala, L-Leu-L-Gln-L-Gln, L-Val-L-Ala-L-Tyr, L-Leu-L-Ala-L-Tyr, L-Leu-L-Ser-L-His or its pharmacologically acceptable acid addition salt, L-Ile-L-Arg-L-Ala or its pharmacologically acceptable acid addition salt, L-Leu-L-Arg-L-Pro or its pharmacologically acceptable acid addition salt, and L-Ile-L-Arg-L-Ala-L-Gln-L-Gln or its pharmacologically acceptable acid addition salt, and a tripeptide represented by the formula L-(or D-) Leu-L-X$_{aa}$-L-Pro wherein X$_{aa}$ is Gly, Ala, Val, Ile, Thr, Asp, Glu, Lys, Orn, Cys, Met, Phe, Tyr, Trp, His or a hydroxyproline residue or a pharmacologically acceptable acid addition salt of the above tripeptide wherein X$_{aa}$ is Lys, Orn, His or Arg, or a pharmacologically acceptable alkali or alkaline earth metal salt, ammonium salt or organic base salt of the tripeptide wherein X$_{aa}$ is Asp or Glu.

DETAILED DESCRIPTION OF THE INVENTION

In the above, the tripeptides represented by the formula L-(or D-) Leu-L-X$_{aa}$-L-Pro are tripeptides obtained by synthesis and the other oligopeptides are oligopeptides existing in α-zein.

In the above, acid addition salts include pharmacologically acceptable acid (inorganic acid or organic acid) addition salts, for example, hydrochloride, hydrobromide, sulfate, nitrate, acetate, benzoate, maleate, fumarate, succinate, tartrate, citrate, oxalate, methanesulfonate, tolunesulfonate, aspartate, glutamate, etc.

Further in the above, alkali and alkaline earth metal and ammonium salts include pharmacologically acceptable ones, for example, sodium, potassium, calcium and ammonium salts, and organic base salts include pharmacologically acceptable ones, for example, pharmacologically acceptable basic amino acid salts such as lysine and ornithine salts.

Oligopeptides used in the invention can be prepared by a process to hydrolyze the corn protein with a specified enzyme, a process to introduce amino acids stepwise by an organically chemical synthetic method, a peptide synthetic process utilizing the reverse reaction of a hydrolaze, a geen engineering process, or the like.

Description is made, first, about a process to hydrolyze a corn protein with an enzyme. Although gluten meal may be used as the raw material corn protein, description is made on the case where α-zein obtained by further purifying it is used. α-zein may either be commercially available one or one separated by a known method from zein separated from gluten meal.

As the enzyme, there can be used an endo type protease such as pappin or thermolysin, and thermolysin is particularly preferred. Thermolysin may either be highly pure one or one of industrial grade (for example, Thermoase (produced by Daiwa Kasei Co., Ltd.)).

Treatment of α-zein with thermolysin is described below. This treatment is usually carried out merely in water or in a buffer (for example, a Tris-HCl buffer or a phosphate buffer). Although the concentration of the protein substrate is not particularly limited so long as it is possible to carry out stirring and mixing, the concentration is preferably in the range of 2 to 20% (w/v), which makes the stirring easy. Although the addition amount of the enzyme thermolysin is varied depending on its titer, it is suitable that the amount is usually 0.01% by weight or more, preferably 0.1 to 10% by weight based on the protein. It is also possible to add part of thermolysin in course of reaction. The pH and temperature of the reaction can be around the optimum pH and optimum temperature of thermolysin, and it is suitable that the pH is 6 to 10, preferably 7 to 8 and the temperature is 30° to 80° C., preferably 60° to 70° C. The pH in course of reaction can, if necessary, be adjusted with an aqueous sodium hydroxide solution, hydrochloric acid or the like.

The reaction time is not definite since it is varied depending on the addition amount of the enzyme, reaction temperature and reaction pH, but it is usually on the order of 1 to 50 hours.

Discontinuance of the hydrolysis reaction can be made according to a known method, for example, according to inactivation of the enzyme either by heating of the hydrolyzate or by pH change with addition of an organic acid such as citric acid or malic acid, an inorganic acid such as hydrochloric acid or phosphoric acid or an alkali such as sodium hydroxide or potassium hydroxide, or according to separation of the enzyme by filtration using an ultrafiltration membrane or the like.

The resulting hydrolyzate solution is then subjected to solid-liquid separation (for example, centrifugation or filtration), the resulting liquid is fractionated by ultrafiltration, gel filtration or the like to obtain liquid containing a fraction having a molecular weight of 10,000 or less. This liquid contains the objective oligopeptides of the invention, and this liquid or its concentrate (for example, freeze-dried product) is further fractionated to obtain each objective oligopeptide.

The above freeze-dried product is herein referred to as hydrolyzed α-zein freeze-dried product, and description is further made below about the case to use it.

The hydrolyzed α-zein freeze-dried product is first subjected either to treatment with an anion exchange resin, for example, a weakly basic anion exchange resin (for example, DEAE-Toyopearl 650 M produced by Toso, Co., Ltd.), or to treatment with a cation exchange resin, for example, a weakly acidic cation exchange resin (for example, SP-Toyopearl 650 M produced by Toso Co., Ltd.).

In the fractionation method to pass the hydrolyzed α-zein freeze-dried product first through an anion exchange resin, respective oligopeptides are fractionated by linear gradient elution (for example, elution with a Tris buffer →NaCl in the Tris buffer, of a suitable concentration, in case of use of DEAE-Toyopearl 650 M). The eluate is taken in several fractions, each of which is then subjected to gel filtration (using, for example, Sephadex LH-20), cation exchange resin treatment (using, for example SP-Toyopearl 650 M), reverse-phase HPLC (using, for example, CAPCELL PAK, $C_{18}$, tradename of octadecylsilane, produced by Shiseido Co., Ltd. or Senshu PAK 1251-Y, tradename of octadecylsilane, produced by Senshu Kagaku Co., Ltd.) and/or the like to factionate it into individual oligopeptides.

Many peptide synthesis methods have hitherto been known, and, for example, are detailedly described in Nobuo Izumiya, Tetsuo Kato, Haruhiko Aoyagi and Michinori Waki, "The Foundations and Experiments of Peptide Synthesis" (Pepuchido Gosei no Kiso to Jikken) published by Maruzen Co., Ltd., Tokyo, 1985, which is incorporated herein for reference.

The oligopeptides used in the invention, particularly the tripeptides of the formula L-(or D-) Leu-L-$X_{aa}$-L-Pro can be prepared by any of these synthetic methods, for example by so-called solid-phase peptide synthesis or liquid-phase peptide synthesis.

The liquid-phase peptide synthesis is described in the above "The Foundations and Experiments of Peptide Synthesis" and can be carried out accordingly, for example by dissolving an amino acid which is to be positioned at the C-terminus of the present oligopeptides and whose carboxyl group is protected with a benzyl group (Bzl), a t-butyl group (t-Bu) or the like, and an amino acid which is to be positioned adjacent to the C-terminal amino acid and whose α-amino group is protected with a t-butyloxycarbonyl group (Boc), a benzyloxycarbonyl group (Z) or the like in dimethylformamide (DMF), dimethylacetamide or the like and reacting them in the presence of dicyclohexylcarbodiimide (DCC) and 1-hydroxybenzotriazole (HOBT) usually at room temperature overnight. Then, the dipeptide obtained after removal of the amino-protecting group of the product by a conventional method is, if necessary, likewise reacted with an amino-protected third amino acid and the amino-protecting group is removed, and the same procedure is, if necessary, repeated to obtain a present oligopeptide. When an amino acid to be reacted has a hydroxyl group, the amino group other than one at the α-position, a carboxyl group other than one at the α-position, a mercapto group, a guanidino group, an imidazolyl group or the like, which should not take part in the reaction, these groups should generally be protected prior to the reaction. Protective groups for an alcoholic hydroxyl group include Bzl, t-Bu, etc., protective groups for a phenolic hydroxyl group include Bzl, etc., protective groups for an amino group other than one at the α-position and for a carboxyl group other than one at the α-position include those mentioned as protective groups for the α-amino group and α-carboxyl group respectively, protective groups for a mercapto group include Bzl, a trityl group, etc., protective groups for a guanidino group include a tosyl group (Tos), etc., protective groups for an imidazolyl group include Tos, etc. Introduction of these protective groups can be carried out by a conventional method, for example as described in the above "The Foundations and Experiments of Peptide Synthesis". After completion of the final reaction, these protective groups are removed, and these deprotections can be carried out by conventional methods, for example as described in the above "The Foundations and Experiments of Peptide Synthesis". For example, as for amino-protecting groups, Boc can be removed by a trifluoro acetic acid (TFA) or formic acid, and Z by catalytic reduction, and as for carboxyl-protecting groups, Bzl can, for example, be removed by catalytic reduction, and t-Bu by TFA or HCl/dioxane. Further, as for alcoholic hydroxyl-protecting groups, Bzl can, for example, be removed by catalytic reduction or HF, and t-Bu by HCl/acetic acid or TFA, and as for phenolic hydroxyl-protecting groups, Bzl by catalytic reduction. Further, as for mercapto-protecting groups, Bzl can, for example, be removed by Na/$NH_3$, and the trityl group by Na/$NH_3$, and as for guanidino and imidazolyl-protecting groups, Tos by Na/$NH_3$ or HF.

On the other hand, as for solid-phase peptide syntheses, those utilizing a peptide synthesizer have recently widely been used, and in the invention the present oligopeptides, particularly the tripeptide of the formula L-(or D-) Leu-L-$X_{aa}$-L-Pro were synthesized using a Model 430 A peptide synthesizer produced by Applied Biosystems Co. Namely, basically, amino acids whose α-amino group is protected with Boc (Boc-amino acid) are extended stepwise by repeat of peptide bonding and removal of Boc from the N-side of, as a starting material, the phenylacetamidomethyl (PAM) resin to which L-Pro, e.g., is linked, i.e., L-Pro-O-CH$_2$-PAM (available from Applied Biosystems Co.). Boc-L-Arg (Mts) (Mts is mesitylene-2-sulfonyl), Boc-L-Asn and Boc-L-Gln are subjected to extension reactin via its 1-hydroxybenzotriazole (HOBT) ester as an intermediate, and the other Boc-amino acids are subjected to extension reaction via its symmetrical anhydride by use of DCC as an intermediate. In the above Boc- amino acids, the reactive functional group, if any, should generally be protected by a suitable protecting group. Examples of protected Boc-amino acids in relation to the invention are Boc-L-Arg (Mts), Boc-L-Asp (OBzl), Boc-L-Cys(4-CH$_3$Bzl) (4-CH$_3$Bzl is 4-methylbenzyl), Boc-L-Glu(OBzl), Boc-L-Lys(Cl-Z) (Cl-Z is 4-brombenzyloxycarbonyl), Boc-L-Ser(Bzl), Boc-L-Thr (Bzl), Box-L-Trp(CHO), Box-L-Tyr(Br-Z) (Br-Z is 4-brombenzyloxycarbonyl), Box-L-His(DNP) (DNP is 2,4-dinitrophenyl), etc. In the synthetic system using the Model 430 A Peptide Synthesizer, the following reagents and solvents are used besides the amino acid materials: N,N-diisopropylethylamine (TFA neutralizer), TFA(Box cleavage), MeOH (dissolution and removal of urea compounds formed), HOBT (0.5M HOBT/DMF), DCC (0.5M DCC/dichloromethane (DCM)), DCM and DMF (solvents), the neutralizer (70% ethanolamine, 29.5% methanol) (neutralization of the waste solution). Amino acid materials and these reagents and solvents are arranged in the prescribed spots. Uses of them are automatically carried out by the peptide synthesizer. Arrangement of the reaction temperature and time is also automatically done, and the reaction temperature is usually room temperature. By the above procedure is obtained an oligopeptide (or tripeptide)-O-CH$_2$-PAM wherein the reactive functional groups in the oligopeptide (or tripeptide) are protected. The actual operation of the above solid-phase peptide synthesis was carried out according to Model 430 A Peptide Synthesizer User's Mannual (Part Number 900066, Version 1.3B, Jul. 1, 1988) by Applied Biosystems Co., which is incorporated herein for reference.

The obtained oligopeptide (or tripeptide)-O-CH$_2$-PAM whose reactive functional groups are protected is treated according to conventional method(s), for example as described in the above "The Foundations and Experiments of Peptide Synthesis" or Model 430 A Peptide Synthesizer User's Mannual, for example with trifluoromethanesulfonic acid (TFMSA) together with TFA, a diluent of TFMSA in the presence of thioanisole and/or ethanedithiol, as scavenger(s), to trap the cation(s) formed by cleavage of the protective group(s) to cleave the resin and the protective group(s) whereby the desired oligopeptide (or tripeptide) is obtained. In the above TFMSA method, when the protected oligopeptide (or tripeptide)-O-CH$_2$-PAM has an L-His(DNP) residue, it is subjected to the above treatment after removal of DNP with thiophenol.

Acid addition salts of the present oligopeptides can be prepared according to a conventional method. For example, an acid addition salt can be obtained by reacting one of the present oligopeptides containing a basic amino acid residue with a suitable acid in one equivalent amount thereto in water and then freeze-drying the product. Further, alkali or alkaline earth metal salts, ammonium salts or organic base salts (hereinafter these are referred to as base salts in view of convenience) can also be prepared according to a conventional method. For example, a base salt can be obtained by reacting one of the present oligopeptides containing an acidic amino acid residue with a suitable base in one equivalent amount thereto in water and then freeze-drying the product.

The present oligopeptides and their acid addition salts or base salts have an ACE inhibiting activity and actually or probably a hypotensive activity, and thus are expected to be effective for treatment and/or prophylaxis of hypertension of mammals including human beings.

The present oligopeptides and their acid addition salts or base salts are used as they are or usually in the form of a pharmaceutical composition comprising one or more of them and at least one pharmaceutical auxiliary.

The present oligopeptides and their acid addition salts or base salts can be administered parenterally (namely, intravenous injection, rectal administration or the like) or orally, and formulated into a form suitable for each administration method.

Pharmaceutical forms for injections usually include sterilized aqueous solutions. Formulations of the above form can further contain pharmaceutical auxiliaries other than water such as a buffering and a pH adjusting agent (sodium hydrogenphosphate, citric acid or the like), a tonicity agent (sodium chloride, glucose or the like), a preservative (methyl p-hydroxybenzoate, propyl p-hydroxybenzoate or the like). The formulations can be sterilized by filtration through a bacteria-holding filter, incorporation of a sterilant into the composition, or irradiation or heating of the composition. The formulations can also be prepared as a sterilizing solid composition and dissolved at the time of use in a sterilized water and used.

Orally administering agents are prepared so that they may have a form suitable for absorption in gastrointestinal organs. Tablets, capsuls, granules, fine granules and powders can contain conventional pharmaceutical auxiliaries, for example, a binder (e.g., syrup, gum arabic, gelatin, sorbitol, tragacanth, polyvinylpyrrolidone or hydroxycellulose), an excipient (e.g., lactose, sucrose, corn starch, calcium stearate, sorbitol or glycine), a lubricant (e.g., magnesium stearate, talc, polyethylene glycol or silica), a disintegrant (potato starch or carboxymethylcellulose), a wetting agent (e.g., sodium lauryl sulfate). Tablets can be coated by a conventional method. Oral liquid agents can be aqueous solutions or the like, or dry products. Such oral liquid agents may contain conventional additives such as a preservative (methyl p-hydroxybenzoate, propyl p-hydroxybenzoate, sorbic acid or the like).

The amount of the present oligopeptide or an acid addition salt or base salt thereof in the present ACE inhibitor or hypotensive agent can variously be varied, but it is suitable that the amount is usually 5 to 100% (w/w), particularly 10 to 60% (w/w). It is suitable that the administration amount of the present ACE inhibitor or hypotensive agent is 10 to 200 mg/kg/day as an amount of the effective ingredient, when administered to a human being. This is also the case with the administration amount of the oligopeptides in the method for inhidition of ACE and in the method for treatment or prophylaxis of hypertensin of the invention. Values of the acute toxicity of the present oligopeptides are generally >3 g/kg in $LD_{50}$ (ICR strain mice, oral administration).

Further, since the present oligopeptides and their acid addition salts or base salts have an advantage that the uptake of a large amount thereof does not have a bad influence on living bodies, they can also be eaten, as they are or together with various nutrients added or a form in which they are contained in foods and drinks, as a functional food or health food which carries a hypotensive activity or the function of prophylaxis of hypotension. Namely, in addition the present oligopeptides can either be formulated, with addition of nutrients such as various vitamins and minerals, into liquid foods such as nutrient drinks, soymilks and soups or solid foods of various shapes, or used as they are in the form of powder orby addition to various foods. The content and ingestion amount of the effective ingredient in the present ACE inhibitor or hypotensive agent as such a functional food or health food can be similar to the content and dose in the above pharmaceutical agent, respectively.

This invention is further described below according to examples.

EXAMPLE 1

(1) Preparation of an α-zein Hydrolyzate Freeze-Dried Product 100 g of α-zein (produced by Wako Pure Chemical Industries, Ltd.) was added to 2,000 ml of distilled water, 1 g of thermolysin (produced by Daiwa Kasei Co., Ltd.) was added, the mixture was warmed from room temperature to 65° C. over a period of 1 hour under stirring, and reaction was carried out at 65° C. for 17 hours. During this reaction the pH was held at 8.0 with appropriate dropwise addition of 5N NaOH. Then, 1 g of thermolysin was further added and the pH was held at 8.0 at 65° C. for 24 hours to carry out rection. In order to inactivate the enzyme the mixture was held at 105° C. for 5 minutes in an autoclave.

The resulting hydrolyzates mixture was centrifuged at 5,000 rpm for 10 minutes, the supernatant was subjected to ultrafiltration using Amicon PM-10 (an ultrafiltration membrane, fractionation molecular weight 10,000, produced by Amicon Co.), and the filtrate was freeze-dried to obtain 97.3 g of an α-zein hydrolyzate freeze-dried product.

(2) 2 g of the thus obtained α-zein hydrolyzate freeze-dried product was dissolved in 2 l of distilled water, the solution was added to a column (2.6×70 cm) of DEAE-Toyopearl 650M, an anion exchange resin, 1,500 ml of a 5 mM Tris buffer (pH 8.3) was flowed, and the nonadsorbed fraction, named Solution A, was recovered. Then, elution was carried out by linear gradient using 1,000 ml of a 5 mM Tris buffer (pH 8.3) and 1,000 ml of a 5 mM Tris buffer (pH 8.3) containing 0.3M NaCl.

The eluate fractions of 320 to 520 ml after the start of elution by the linear gradient were named Solution B, and the eluate fractions of 620 to 700 ml thereafter were named Solution C.

(3) Treatment of Fraction A

Solution A after freeze-drying was added to a column (1.6×100 cm) of Sephadex LH-20, a gel filtration resin produced by Pharmacia Co. and elution was earried out with 30% methanol to conduct desalting. Solution A after the desalting was then added to a column (2.6×70 cm) of SP-Toyopearl 650M, a cation exchange resin, and, after flowing 500 ml of a 5 mM sodium acetate buffer (pH 4.0), elution was carried out by linear gradient using 1,000 ml of a 5 mM sodium acetate buffer (pH 4.0) and 1,000 ml of a 5 mM sodium acetate buffer (pH 4.0) containing 0.6M NaCl. The eluate fractions of 340 to 600 ml after the start of elution by concentration gradient was named Solution A1, and the eluate fractions of 950 to 1050 ml thereafter Solution A2.

Solution A1 was further fractionated using a semi-preparative high performance liquid chromatograph produced (hereinafter likewise) by Japan Millipore Limited Co. The elution conditions are as follows:

Column: CAPCELL PAK C18 (1.5×25 cm).
Eluent: Gradient of 10 to 60% acetonitrile in the presence of 0.1% trifluoroacetic acid (hereinafter abbreviated as TFA) (running time: 30 minutes).
Flow rate: 8 ml/min.
Detection: UV 210 nm.

Under these conditions the eluate fractions of 4.0 to 6.3 minutes, 6.3 to 7.7 minutes and 9.1 to 9.3 minutes were named A1-1, A1-2 and A1-3, respectively.

A1-1 was further fractionated using the semi-preparative high performance liquid chromatograph.

Elution conditions therefor are as follows:
Column: CAPCELL PAK C18 (1.5×25 cm).
Eluent: Gradient of 0 to 20% acetonitrile in the presence of 0.1% TFA (running time: 20 minutes).
Flow rate: 8 ml/min.
Detection: UV 210 nm.

Under these conditions the eluate fractions of 14.3 to 14.5 minutes were named A1-1-1. A1-2 was further fractionated by the semi-preparative high performance liquid chromatograph. Elution conditions therefor are as follows:

Column: CAPCELL PAK C18 (1.5×25 cm).
Eluent: Gradient of 0 to 20% acetonitrile in the presence of 0.1% TFA (running time: 20 minutes).
Flow rate: 8 ml/min.
Detection: UV 210 nm.

Under these conditions the eluate fractions of 14.9 to 15.1 minutes and 16.9 to 17.1 minutes were named A1-2-1 and A1-2-2, respectively.

Solution A2 was further fractionated by the semi-preparative high performance liquid chromatograph. Elution conditions therefor are as follows:

Column: CAPCELL PAK C18 (1.5×25 cm).
Eluent: Gradient of 0 to 20% acetonitrile in the presence of 0.1% TFA (running time: 20 minutes).
Flow rate: 8 ml/min.
Detection: UV 210 nm.

Under these conditions the eluate fractions of 14.9 to 15.1 minutes were named A2-1.

(4) Treatment of Fraction B

The aforesaid solution B was fractionated, after freeze drying, by the semi-preparative high performance liquid chromatograph.

Elution conditions therefor are as follows:
Column: CAPCELL PAK C18 (1.5×25 cm).

Eluent: Gradient of 10 to 60% acetonitrile in the presence of 0.1% TFA (running time: 30 minutes)

Flow rate: 8 ml/min.

Detection: UV 210 nm.

Under these conditions the eluate fractions of 6.8 to 7.8 minutes, 7.8 to 8.3 minutes, 8.3 to 9.1 minutes and 14.2 to 14.4 minutes were named B1, B2, B3 and B4, respectively.

B1 was further fractionated by the semi-preparative high performance liquid chromatograph. Elution conditions therefor are as follows:

Column: CAPCELL PAK C18 (1.5×25 cm).

Eluent: 10% acetonitrile in the presence of 0.1% TFA

Flow rate: 8 ml/min.

Detection: UV 210 nm.

Under these conditions the eluate fractions of 6.9 to 7.1 minutes were named B1-1.

B2 was further fractionated by the semi-preparative high performance liquid chromatograph. Elution conditions therefor are as follows:

Column: CAPCELL PAK C18 (1.5×25 cm).

Eluent: 10% acetonitrile in the presence of 0.1% TFA

Flow rate: 8 ml/min.

Detection: UV 210 nm.

Under these conditions the eluate fractions of 11.2 to 11.4 minutes were named B2-1.

B3 was further fractionated by the semi-preparative high performance liquid chromatograph. Elution conditions therefor are as follows:

Column: CAPCELL PAK C18 (1.5×25 cm).

Eluent: 10% acetonitrile in the presence of 0.1% TFA

Flow rate: 8 ml/min.

Detection: UV 210 nm.

Under these conditions the eluate fractions of 15.0 to 16.0 minutes were named B3-1.

(5) Treatment of Fraction C

The above Solution C was added, after freeze-drying, to a column (1.6×100 cm) of Sephadex LH-20, a gel filtration resin, and eluted with 30% methanol to desalt it. Solution C after the desalting was further fractionated by the semi-preparative high performance liquid chromatograph. Elution conditions therefor are as follows:

Column: CAPCELL PAK C18 (1.5×25 cm).

Eluent: Gradient of 10 to 60% acetonitrile in the presence of 0.1% TFA (running time: 30 minutes).

Flow rate: 8 ml/min.

Detection: UV 210 nm.

Under these conditions the eluate fractions of 17.6 to 17.8 minutes were named C1.

(6) Identification of the peptides

All the eluate fractions of the above A1-1-1, A1-2-1, A1-3, A2-1, B1-1, B2-1, B3-1, B4 and C1 exhibited a single peak by the above high performance liquid chromatography.

These eluate fractions were then evaporated to dryness and dissolved in distilled water, and the following structural analyses were made using these aqueous solutions.

Table 1 shows amino acid analytical values after hydrolysis with 6N hydrochloric acid at 110° C. for 24 hours (by a Hitachi L-8500 type amino acid analyzer), mass spectrum values (by JEOL. JMX-DX 303) and amino acid sequence analytical data (by a Shimadzu protein sequencer PSQ-1 system).

EXAMPLE 2

(1) 2 g of an α-zein hydrolyzate freeze-dried product prepared in the same manner as in Example 1 (1) was dissolved in a 0.02M aqueous acetic acid solution, and the solution was adjusted to 500 ml in volume and pH 4.0. The resulting solution was added to a column (2.6×76 cm) of a cation exchange resin SP-Toyopearl 650M, and 1,500 ml of a 0.02M ammonium acetate buffer (pH 4.0) was flowed to remove the nonadsorbed fraction. Then, elution was carried out by linear gradient using 1,000 ml of a 0.02M ammonium acetate buffer (pH 4.0) and 1,000 ml of a 500M ammonium acetate buffer (pH 8.6), and successively using a 0.05M ammonium acetate buffer (pH 8.6).

The eluate fractions of 850 to 1,000 ml, 1,000 to 1,100 ml, 1,100 to 1,200 ml, 1,400 to 1,500 ml, 1920 to 2,120 ml and 2,200 to 2,270 ml were named Solutions D, E, F, G, H and L, respectively.

(2) Treatment of Fraction D

The above Solution D was fractionated, after freeze-drying, by the semi-preparative high performance liquid chromatograph. Elution conditions therefor are as follows:

Column: CAPCELL PAK C18 (1.5×25 cm).

Eluent: Gradient of 10 to 60% acetonitrile in the presence of 0.1% TFA (running time: 30 minutes).

Flow rate: 8 ml/min.

Detection: UV 210 nm.

Under these conditions the eluate fractions of 10.5 to 11.0 minutes were named D1.

(3) Treatment of Fraction E

The above Solution E was fractionated, after freeze-drying, by the semi-preparative high performance liquid chromatograph. Elution conditions therefor are as follows:

Column: CAPCELL PAK C18 (1.5×25 cm).

Eluent: Gradient of 10 to 60% acetonitrile in the presence of 0.1% TFA (running time: 30 minutes).

Flow rate: 8 ml/min.

Detection: UV 210 nm.

Under these conditions the eluate fractions of 13.0 to 13.2 minutes were named E1.

(4) Treatment of Fraction F

The above Solution F was fractionated, after freeze-drying, by the semi-preparative high performance liquid chromatograph. Elution conditions therefor are as follows:

Column: CAPCELL PAK C18 (1.5×25 cm).

Eluent: Gradient of 10 to 60% acetonitrile in the presence of 0.1% TFA (running time: 30 minutes).

Flow rate: 8 ml/min.

Detection: UV 210 nm.

Under these conditions the eluate fractions of 10.3 to 10.7 minutes, 12.5 to 13.2 minutes and 17.0 to 18.0 minutes were named F1, F2 and F3, respectively.

(5) Treatment of Fraction G

The above Solution G was fractionated, after freeze-drying, by the semi-preparative high performance liquid chromatograph. Elution conditions therefor are as follows:

Column: CAPCELL PAK C18 (1.5×25 cm).

Eluent: Gradient of 10 to 60% acetonitrile in the presence of 0.1% TFA (running time: 30 minutes).
Flow rate: 8 ml/min.
Detection: UV 210 nm.
Under these conditions the eluate fractions of 5.0 to 5.2 minutes and 13.8 to 15.0 minutes were named G1 and G2, respectively.

(6) Treatment of Fraction H

The above Solution H was fractionated, after freeze-drying, by the semi-preparative high performance liquid chromatograph. Elution conditions therefor are as follows:
Column: CAPCELL PAK C18 (1.5×25 cm).
Eluent: Gradient of 10 to 60% acetonitrile in the presence of 0.1% TFA (running time: 30 minutes).
Flow rate: 8 ml/min.
Detection: UV 210 nm.
Under these conditions the eluate fractions of 7.7 to 8.7 minutes and 9.6 to 9.9 minutes were named H1 and H2, respectively.

H2 was further fractionated by the semi-preparative high performance liquid chromatograph. Elution conditions therefor are as follows:
Column: CAPCELL PAK C18 (1.5×25 cm).
Eluent: 10% acetonitrile in the presence of 0.1% TFA
Flow rate: 8 ml/min.
Detection: UV210 nm
Under these conditions the eluate fractions of 12.6 to 13.2 minutes were named H2-1.

(7) Treatment of Fraction I

The above Solution I was fractionated, after freeze-drying, by the semi-preparative high performance liquid chromatograph. Elution conditions therefor are as follows:
Column: CAPCELL PAK C18 (1.5×25 cm).
Eluent: Gradient of 10 to 60% acetonitrile in the presence of 0.1% TFA (running time: 30 minutes).
Flow rate: 8 ml/min.
Detection: UV 210 nm.
Under these conditions the eluate fractions of 6.5 to 7.2 minutes are named I1.

(8) Identification of the Peptides

The structural analyses of each of the above eluate fractions were carried out in the same manner as in Example 1 (6).
The results are shown in Table 1.

EXAMPLE 3

Synthesis of L-Leu-L-Ala-L-Pro 0.5 mmol of a Boc-L-Pro-O-CH$_2$-PAM resin and 2 mmol each of Boc-L-Ala and Boc-L-Leu were charged into a peptide synthesizer (Model 430 A) (produced by Applied Biosystems Co.), equipped with N,N-diisopropylamine, TFA, MeOH, 0.5M HOBT/DMF, 0.5M DCC/DCM, DCM, DMF and the neutralyzer (70% ethanolamine+29.5% methanol), and subjected to the anhydride symmetrical method with DCC to synthesize Boc-L-Leu-L-Ala-L-Pro-O-CH$_2$-PAM which was then vacuum dried.

1 g of the dried peptide resin, 1 ml of thioanisole and 500 ml of ethanedithiol were placed in a 100-ml round bottom flask, and the mixture was stirred for 10 minutes. 10 ml of TFA was gradually added to the mixture while the flask was cooled with ice water, and the resulting mixture was stirred for 10 minutes. 1 ml of TFMSA was gradually added, the flask was taken out from ice water, and reaction was continued at room temperature for 30 minutes with stirring cold diethl ether (about 50 ml) was added until no precipitate of the peptide came to be newly formed, followed by 1 minute stirring. The while contents of the flask was transferred onto a glass filter (medium porosity) and washed with cold diethyl ether. A beaker containing about 200 ml of cold diethyl was placed under the glass filter, and stirring was started. The peptide was dissolved with addition of TFA to the glass filter and transferred into the ether (precipitate of the peptide was formed in the ether). Addition of TFA was continued until no precipitate came to be newly formed. The peptide precipitate in the ether was transferred onto a glass filter (medium porosity), filtered and washed several times with diethyl ether. The peptide or the glass filter was then dissolved in 2N acetic acid and collected into an agg-plant type flask. The solution was freeze dried. The freeze dried product was dissolved in distilled water and purified by semi-preparative high performance liquid chromatograph. Elution conditions therefor are as follows:
Column: CAPCELL PAK C18 (1.5×25 cm).
Eluent: Gradient of 5 to 80% acetonitrile in the presence of 0.1% trifluoroacetic acid (running time: 45 minutes).
Flow rate: 8 ml/min.
Detection: UV 210 nm.
The eluate fractions containing the main peak by the detection were concentrated to dryness under reduced pressure, the residue was redissolved in a 2N aqueous acetic acid solution, and the solution was freeze-dried.

By this process 2 mg of L-Leu-L-Ala-L-Pro was obtained as powder (The results of the various analyses are shown in later Table 1, and this is applied likewise hereinafter).

EXAMPLE 4

Synthesis of L-Leu-L-Lys-L-Pro 0.5 mmol of a Boc-L-Pro-O-CH$_2$-PAM resin and 2 mmol each of Boc-L-Lys(Z) and Boc-L-Leu were charged into the peptide synthesizer equipped as in Example 3 and subjected to the anhydride symmetrical method with DCC to synthesize Boc-L-Leu-L-Lys(Z)-L-Pro-O-CH$_2$-PAM.

Then, the same operation as in Example 3 was carried out to obtain 90 mg of L-Leu-L-Lys-L-Pro as powder.

EXAMPLE 5

Synthesis of L-Leu-L-His-L-Pro 0.5 mmol of a Boc-L-Pro-O-CH$_2$-PAM resin and 2 mmol each of Boc-L-His (DNP) and Boc-L-Leu were charged into the peptide synthesizer equipped as in Example 3 and subjected to the anhydride symmetrical method to synthesize Boc-L-Leu-L-His (DNP)-L-Pro-O-CH$_2$-PAM.

1 g of the vacuum dried peptide resin, 1 ml of thiophenol and 24 ml of DMF were placed in a 100 ml round bottom flask, and stirred at room temperature for 30 minutes to carry out reaction. After the reaction, the resin was filtered with a glass filter (medium porosity) and washed several times with diethyl ether. After drying, the peptide resin wherein DNP was eliminated was subjected to the same de-Boc operation as in Example 3 to obtain 110 mg of L-Leu-L-His-L-Pro as powder.

EXAMPLE 6

Synthesis of L-Leu-L-Thr-L-Pro

The operations of Example 3 were repeated except that 2 mmol of Box-L-Thr(Bzl) was used in place of 2 mmol of Boc-L-Ala to obtain 2 mg of L-Leu-L-Thr-L-Pro as powder.

EXAMPLE 7

Synthesis of L-Leu-L-Glu-L-Pro

The operations of Example 3 were repeated except that 2 mmol of Boc-L-Glu(OBzl) was used in place of 2 mmol of Boc-L-Ala to obtain 3.5 mg of L-Leu-L-Glu-L-Pro as powder.

EXAMPLE 8

Synthesis of L-Leu-L-Asp-L-Pro

The operations of Example 3 were repeated except that 2 mmol of Boc-L-Asp(OBzl) was used in place of 2 mmol of Boc-L-Ala to obtain 5.8 mg of L-Leu-L-Asp-L-Pro as powder.

EXAMPLE 9

Synthesis of L-Leu-Gly-L-Pro

The operations of Example 3 were repeated except that 2 mmol of Boc-Gly was used in place of 2 mmol of Boc-L-Ala to obtain 7 mg of L-Leu-Gly-L-Pro as powder.

EXAMPLE 10

Synthesis of L-Leu-L-Tyr-L-Pro

The operations of Example 3 were repeated except that 2 mmol of Boc-L-Tyr(Br-Z) was used in place of 2 mmol of Boc-L-Ala to obtain 7 mg of L-Leu-L-Tyr-L-Pro as powder.

EXAMPLE 11

0.5 mmol of a Boc-L-Pro-O-CH$_2$-PAM resin and 2 mmol each of Boc-L-Arg(Mts) and Boc-D-Leu were charged into the peptide synthesizer equipped as in Example 3, and subjected to the active ester method with HOBT to synthesize Boc-D-Leu-L-Arg (Mts)-L-Pro-O-CH$_2$-PAM which was then vacuum dried. The dried peptide resin (1 g) was then treated in the same manner as in Example 3 to obtain 120 mg of D-Leu-L-Arg-L-Pro as powder.

EXAMPLE 12

Synthesis of L-Leu-L-Arg-L-Pro 0.5 mmol of a Boc-L-Pro-O-CH$_2$-PAM resin and 2 mmol each of Boc-L-Arg(Mts) and Boc-L-Leu were charged into the peptide synthesizer equipped as in Example 3 and subjected to the active ester method with HOBT to synthesize Boc-L-Leu-L-Arg (Mts)-L-Pro-O-CH$_2$-PAM which was then vacuum dried. The dried peptide resin (1 g) was then treated in the same manner as in Example 3 to obtain 100 mg of L-Leu-L-Arg-L-Pro as powder.

EXAMPLE 13

ACE Inhibition Activity

The ACE inhibition activity of the thus obtained present oligopeptides was measured as follows. Namely, first, 5 g of rabbit lung acetone powder was dissolved in 50 ml of 0.1M sodium borate buffer (pH 8.3), the solution was centrifuged under the conditions of 40,000 G for 40 minutes, and the supernatant was further purified with hydroxyapatite to obtain an angiotensin converting enzyme solution having an enzyme activity of 1 unit/mg protein.

0.03 ml portions of aqueous solutions containing in various concentrations any one of the present oligopeptides was placed in test tubes, 0.25 ml portions of hippuroylhistidylleucine (final concentration 5 mM; containing 300 mM NaCl) were added thereto, 0.1 ml portions of the above angiotensin converting enzyme solution were added, and reactions were carried out at 37° C. for 30 minutes. Thereafter, 0.25 ml portions of 1N hydrochloric acid were added to discontinue the reactions, 1.5 ml portions of ethyl acetate were added, the absorbances of hippuric acid, which was extracted in the ethyl acetate extractions, were measured at 228 nm as an enzyme activity. The absorbance at 228 nm under these conditions when the present oligopeptide was not contained was 0.35.

Plural of such an experiment were conducted and the inhibition rate was calculated by the following equation:

$$\text{Inhibition rate} = \frac{A - B}{A} \times 100\ (\%)$$

A: Absorbance at 228 nm when the inhibitor was not contained

B: Absorbance at 228 nm when the inhibitor was added

The concentration of the present oligopeptide at the inhibition rate of 50% was referred to as an IC$_{50}$ value.

The results are shown in Table 1.

EXAMPLE 14

Hypotensive Activity 10-week old spontaneous hypertensive rats (SHR) (produced BY Nihon Rat Co., Ltd., ♂, weight 240 to 280 g, 4 to 6 animals per 1 group) were used as test animals. L-Leu-L-Arg-L-Pro obtained as in Example 12 was dissolved in physiological saline and 120 mg in terms of the effective ingredient of the solution was intraperitoneally administered per kg of animal. As control physiological saline was intraperitoneally administered. Blood pressure was measured before the administration and at regular intervals of time after the administration by the Tail-Cuff method using a bloodless sphygmomanometer for rats and mice TK-350 (produced by Unicom Co., Ltd.)

The results were shown in Table 2 by (Maximum blood pressure value before the administration-Maximum blood pressure value after the administration) ± S.E.

TABLE 2

| Test sample | Lowering of blood pressure (mm Hg) 5 hours later |
|---|---|
| Rhysiological saline | −1 ± 3 |
| L—Leu—L—Arg—L—Pro | 14 ± 5* |

*There is significance against the control by p < 0.01

EXAMPLE 15

Intravenous Injection

A present oligopeptide or pharmacologically acceptable addition or base salt thereof is dissolved in 20 to 100 times (volume/weight) of sterilized physiological saline, and the solution is aseptically filtered through a filter (poresize: 0.45 μm), and the resulting filtrate is used as an injection.

EXAMPLE 16

Tablet

| Tablet | |
|---|---|
| A present oligopeptide or pharmacologically acceptable addition or base salt thereof | 7 parts |
| Hydroxypropylcellulose | 1 part |
| Lactose | 10.9 parts |
| Potato starch | 1 part |
| Magnesium stearate | 0.1 part |

20 parts of an aqueous 60% ethanol solution containing 1 part of hydroxypropylcellulose is prepared, 7 parts of the oligopeptide and 10.9 parts of lactose are added, the mixture is sufficiently kneaded and dried under reduced pressure, 1 part of potato starch and 0.1 part of magnesium stearate are added to the dried product, and the mixture is mixed and formulated into tablets by a tableting machine.

TABLE 1

Analytical value of oligopeptides either derived from corn or synthesized

| Eluate fraction | Amino acid sequence | Amino acid analytical value | Mass spectrum | Concentration giving the inhibition rate | $IC_{50}$ or (μM) |
|---|---|---|---|---|---|
| A1-1-1 | L—Leu—L—Gln—L—Gln | Leu(1.00) Glu(1.92) | $388(M + H)^+$ | $IC_{50}$ | 100 |
| A1-2-1 | L—Val—L—Ala—L—Ala | Val(1.00) Ala(2.11) | $260(M + H)^+$ | $IC_{50}$ | 13 |
| A1-2-2 | L—Val—L—Ser—Ser—L—Pro | Val(1.02) Ser(1.06) Pro(1.00) | $302(M + H)^+$ | $IC_{50}$ | 10 |
| A1-3 | L—Leu—L—Asn—L—Pro | Leu(1.02) Asp(1.05) Pro(1.00) | $343(M + H)^+$ | $IC_{50}$ | 35 |
| A2-1 | L—Ile—Arg—L—Ala—L—Gln—L—Gln | Ile(1.00) Arg(0.93) Ala(1.06) Glu(2.04) | $615(M + H)^+$ | $IC_{50}$ | 160 |
| B1-1 | L—Leu—L—Ala—L—Ala | Leu(1.00) Ala(1.80) | $274(M + H)^+$ | $IC_{50}$ | 13 |
| B2-1 | L—Leu—L—Gln—L—Pro | Leu(1.09) Glu(0.93) Pro(1.00) | $357(M + H)^+$ | $IC_{50}$ | 1.9 |
| B3-1 | L—Leu—L—Ser—L—Pro | Leu(1.06 Ser(0.91) Pro(1.00) | $316(M + H)^+$ | $IC_{50}$ | 1.7 |
| B4 | L—Leu—L—Leu—L—Pro | Leu(1.93) Pro(1.00) | $342(M + H)^+$ | $IC_{50}$ | 57 |
| C1 | L—Phe—L—Leu—L—Pro | Phe(1.00) Leu(1.10) Pro(0.99) | $376(M + H)^+$ | $IC_{50}$ | 210 |
| D1 | L—Val—L—Ala—L—Tyr | Ala(1.00) Val(1.13) Tyr(0.94) | $352(M + H)^+$ | $IC_{50}$ | 16 |
| E1 | L—Leu—L—Ala—L—Tyr | Ala(1.00) Leu(1.07) Tyr(0.88) | $366(M + H)^+$ | $IC_{50}$ | 3.9 |
| F1 | L—Tyr—L—Val | Val(1.03) Tyr(1.00) | $281(M + H)^+$ | 40% | 32 |
| F2 | L—Leu—L—Tyr | Tyr(1.00) Leu(1.01) | $295(M + H)^+$ | 58% | 150 |
| F3 | L—Leu—L—Phe | Leu(1.10) Phe(1.00) | $279(M + H)^+$ | 48% | 600 |
| G1 | L—Leu—L—Ser—L—His | Ser(0.86) Leu(1.00) His(1.06) | $356(M + H)^+$ | 51% | 79 |
| G2 | L—Phe—L—Tyr | Phe(1.03) Tyr(1.00) | $329(M + H)^+$ | $IC_{50}$ | 25 |
| H1 | L—Ile—L—Arg—L—Ala | Ala(1.04) Ile(1.00) Arg(0.94) | $359(M + H)^+$ | $IC_{50}$ | 6.4 |
| H2-1 | L—Leu—L—Arg—L—Pro | Leu(1.10) Arg(1.00) Pro(1.00) | $385(M + H)^+$ | $IC_{50}$ | 0.27 |
| I1 | L—Tyr—L—Arg | Tyr(1.00) Arg(1.03) | $338(M + H)^+$ | 58% | 290 |
| | L—Leu—L—Ala—L—Pro | Leu(1.02) Ala(1.06) Pro(1.00) | $300(M + H)^+$ | 50% | 1.4 |
| | L—Leu—L—Lys—L—Pro | Leu(1.00) Lys(0.95) Pro(1.03) | $357(M + H)^+$ | 50% | 0.6 |

TABLE 1-continued

Analytical value of oligopeptides either derived from corn or synthesized

| Eluate fraction | Amino acid sequence | Amino acid analytical value | Mass spectrum | Concentration giving the inhibition rate | IC$_{50}$ or ($\mu$M) |
|---|---|---|---|---|---|
| | L—Leu—L—His—L—Pro | Leu(1.06) His(1.00) Pro(0.98) | 366(M + H)$^+$ | 50% | 80 |
| | L—Leu—L—Thr—L—Pro | Leu(1.00) Thr(0.91) Pro(1.09) | 330(M + H)$^+$ | 54% | 3.4 |
| | L—Leu—L—Glu—L—Pro | Leu(1.05) Glu(1.00) Pro(0.90) | 358(M + H)$^+$ | 53% | 24 |
| | L—Leu—L—Asp—L—Pro | Leu(1.00) Asp(1.02) Pro(0.97) | 344(M + H)$^+$ | 18% | 182 |
| | L—Leu—Gly—L—Pro | Leu(1.00) Gly(0.95) Pro(1.11) | 286(M + H)$^+$ | 69% | 60 |
| | L—Leu—L—Tyr—L—Pro | Leu(1.00) Tyr(0.86) Pro(1.04) | 392(M + H)$^+$ | 73% | 12 |
| | D—Leu—L—Arg—L—Pro | Leu(1.00) Arg(0.93) Pro(1.11) | 385(M + H)$^+$ | 35% | 45 |

What is claimed is:

1. A compound selected from the group consisting of L-Leu-L-Ser-L-Pro, L-Leu-L-Gln-L-Pro, L-Val-L-Ser-L-Pro, L-Leu-L-Leu-L-Pro, L-Leu-L-Asn-L-Pro, L-Phe-L-Leu-L-Pro, L-Leu-L-Ala-L-Ala, L-Val-L-Ala-L-Ala, L-Leu-L-Gln-L-Gln, L-Val-L-Ala-L-Tyr, L-Leu-L-Ala-L-Tyr, L-Leu-L-Ser-L-His or its pharmacologically acceptable acid addition salt, L-Ile-L-Arg-L-Ala or its pharmacologically acceptable acid addition salt, L-Leu-L-Arg-L-Pro or its pharmacologically acceptable acid addition salt, and L-Ile-L-Arg-L-Ala-L-Gln-L-Gln or its pharmacologically acceptable acid addition salt and a tripeptide represented by the formula L-(or D-) Leu-L-X$_{aa}$-L-Pro wherein X$_{aa}$ is Gly, Ala, Val, Ile, Thr, Asp, Glu, Lys, Orn, Cys, Met, Phe, Tyr, Trp, His or a hydroxyproline residue, or a pharmacologically acceptable acid addition salt of the tripeptide wherein X$_{aa}$ is Lys, Orn, His or Arg and a pharmacologically acceptable alkali or alkaline earth metal salt, ammonium salt or organic base salt of the tripeptide wherein X$_{aa}$ is Asp or Glu.

2. A compound of claim 1 which is selected from the group consisting of L-Val-L-Ala-L-Ala, L-Val-L-Ala-L-Ala, L-Val-L-Ser-L-Pro, L-Leu-L-Asn-L-Pro, L-Leu-L-Ala-L-Ala, L-Leu-L-Gln-L-Pro, L-Leu-L-Ser-L-Pro, L-Leu-L-Leu-L-Pro, L-Val-L-Ala-L-Tyr, L-Leu-L-Ala-L-Tyr, L-Ile-L-Arg-L-Ala or its pharmacologically acceptable acid addition salt, L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, L-Leu-L-Thr-L-Pro, L-Leu-L-Glu-L-Pro or its pharmacologically acceptable alkali or alkaline earth metal salt, ammonium salt or organic base salt, L-Leu-L-Tyr-L-Pro, and D-Leu-L-Arg-L-Pro or its pharmacologically acceptable acid addition salt.

3. A compound of claim 1, which is selected from the group consisting of L-Leu-L-Gln-L-Pro, L-Leu-L-Ser-L-Pro, L-Leu-L-Ala-L-Tyr, L-Ile-L-Arg-L-Ala or its pharmacologically acceptable acid addition salt, L-Leu-L-Arg-L-Pro or its pharmacologically acceptable acid addition salt, L-Leu-L-Lys-L-Pro and its pharmacologically acceptable acid addition salt, L-Leu-L-Ala-L-Pro, and L-Leu-L-Thr-L-Pro.

4. An angiotensin converting enzyme inhibitor which either comprises at least one member which is selected from the group consisting of L-Leu-L-Ser-L-Pro, L-Leu-L-Gln-L-Pro, L-Val-L-Ser-L-Pro, L-Leu-L-Leu-L-Pro, L-Leu-L-Asn-L-Pro, L-Phe-L-Leu-L-Pro, L-Leu-L-Ala-L-Ala, L-Val-L-Ala-L-Ala, L-Leu-L-Gln-L-Gln, L-Val-L-Ala-L-Tyr, L-Leu-L-Ala-L-Tyr, L-Leu-L-Ser-L-His or its pharmacologically acceptable acid addition salt, L-Ile-L-Arg-L-Ala or its pharmacologically acceptable acid addition salt L-Leu-L-Arg-L-Pro or its pharmacologically acceptable acid addition salt, L-Ile-L-Arg-L-Ala-L-Gln-L-Gln or its pharmacologically acceptable acid addition salt, and a tripeptide represented by the formula L-(or D-) Leu-L-X$_{aa}$-L-Pro wherein X$_{aa}$ is Gly, Ala, Val, Ile, Thr, Asp, Glu, Lys, Orn, Cys, Met, Phe, Tyr, Trp, His or a hydroxyproline residue or a pharmacologically acceptable acid addition salt of the tripeptide wherein X$_{aa}$ is Lys, Orn, His or Arg, or a pharmacologically acceptable alkali or alkaline earth metal salt, ammonium salt or organic base salt of the tripeptide wherein X$_{aa}$ is Asp or Glu, and is in an amount effective to inhibit the angiotensin converting enzyme of a human being or another mammal, and, if needed, pharmaceutically acceptable carrier(s)

5. The angiotensin converting enzyme inhibitor of claim 4 wherein said at least one member is selected from the group consisting of L-Val-L-Ala-L-Ala, L-Val-L-Ala-L-Ala, L-Val-L-Ser-L-Pro, L-Leu-L-Asn-L-Pro, L-Leu-L-Ala-L-Ala, L-Leu-L-Gln-L-Pro, L-Leu-L-Ser-L-Pro, L-Leu-L-Leu-L-Pro, L-Val-L-Ala-L-Tyr, L-Leu-L-Ala-L-Tyr, L-Ile-L-Arg-L-Ala or its pharmacologically acceptable acid addition salt, L-Leu-L-Arg-L-Pro or its pharmacologically acceptable acid addition salt, L-Leu-L-Lys-L-Pro or its pharmacologically acceptable acid addition salt, L-Leu-L-ala-L-Pro, L-Leu-L-Thr-L-Pro, L-Leu-L-Glu-L-Pro or its pharmacologically acceptable alkali or alkaline earth metal salt, ammonium salt or organic base salt, L-Leu-L-Tyr- L-Pro, and D-Leu-L-Arg-L-Pro or its pharmacologically acceptable acid addition salt.

6. The angiotensin converting enzyme inhibitor of claim 4 wherein said at least one member is selected from the group consisting of L-Leu-L-Gln-L-Pro, L-Leu-L-Ser-L-Pro, L-Leu-L-Ala-L-Tyr, L-Ile-L-Arg-L-Ala or its pharmacologically acceptable acid addition salt, L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, and L-Leu-L-Thr-L-Pro.

7. A hypotensive pharmaceutical composition for human being or another mammal which either comprises a hypotensively effective amount of at least one member selected from the group consisting of L-Leu-L-Ser-L-Pro, L-Leu-L-Gln-L-Pro, L-Val-L-Ser-L-Pro, L-Leu-L-Leu-L-Pro, L-Leu-L-Asn-L-Pro, L-Phe-L-Leu-L-Pro, L-Leu-L-Ala-L-Ala, L-Val-L-Ala-L-Ala, L-Leu-L-Gln-L-Gln, L-Val-L-Ala-L-Tyr, L-Leu-L-Ala-L-Tyr, L-Leu-L-Ser-L-His or its pharmacologically acceptable acid addition salt, L-Ile-L-Arg-L-Ala or its pharmacologically acceptable acid addition salt, L-Leu-L-Arg-L-Pro or its pharmacologically acceptable acid addition salt, and L-Ile-L-Arg-L-Ala-L-Gln-L-Gln or its pharmacologically acceptable acid addition salt, and a tripeptide represented by the formula L-(or D-) Leu-L-$X_{aa}$-L-Pro wherein $X_{aa}$ is Gly, Ala, Val, Ile, Thr, Asp, Glu, Lys, Orn, Cys, Met, Phe, Tyr, Trp, His or a hydroxyproline residue or a pharmacologically acceptable acid addition salt of the tripeptide wherein $X_{aa}$ is Lys, Orn, His or Arg, or a pharmacologically acceptable alkali or alkaline earth metal salt, ammonium salt or organic base salt of the tripeptides wherein $X_{aa}$ is Asp or Glu, and if needed, pharmaceutically acceptable carrier(s).

8. The composition of claim 7 wherein said at least one member is selected from the group consisting of L-Val-L-Ala-L-Ala, L-Val-L-L-Ala-L-Ala, L-Val-L-Ser-L-Pro, L-Leu-L-Asn-L-Pro, L-Leu-L-Ala-L-Ala, L-Leu-L-Gln-L-Pro, L-Leu-L-Ser-L-Pro, L-Leu-L-Leu-L-Pro, L-Val-L-Ala-L-Tyr, L-Leu-L-Ala-L-Tyr, L-Ile-L-Arg-L-Ala or its pharmacologically acceptable acid addition salt, and L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, L-Leu-L-Thr-L-Pro, L-Leu-L-Glu-L-Pro or its pharmacologically acceptable alkali or alkaline earth metal salt, ammonium salt or organic base salt, L-Leu-L-Tyr-L-Pro, and D-Leu-L-Arg-L-Pro or its pharmacologically acceptable acid addition salt.

9. The composition of claim 7 wherein said at least one member is selected from the group consisting of L-Leu-L-Gln-L-Pro, L-Leu-L-Ser-L-Pro, L-Leu-L-Ala-L-Tyr, L-Ile-L-Arg-L-Ala or its pharmacologically acceptable acid addition salt, and L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, and L-Leu-L-Thr-L-Pro.

10. A method for inhibition of the angiotensin converting enzyme in the body of a human being or another mammal which comprises administering to the human being or another mammal at least one member which is selected from the group consisting of L-Tyr-L-Val, L-Leu-L-Tyr, L-Leu-L-Phe, L-Phe-L-Tyr, L-Tyr-L-Arg or its pharmacologically acceptable acid addition salt, L-Leu-L-Ser-L-Pro, L-Leu-L-Gln-L-Pro, L-Val-L-Ser-L-Pro, L-Leu-L-Leu-L-Pro, L-Leu-L-Asn-L-Pro, L-Phe-L-Leu-L-Pro, L-Leu-L-Ala-L-Ala, L-Val-L-Ala-L-Ala, L-Leu-L-Gln-L-Gln, L-Val-L-Ala-L-Tyr, L-Leu-L-Ala-L-Tyr, L-Leu-L-Ser-L-His or its pharmacologically acceptable acid addition salt, L-Ile-L-Arg-L-Ala or its pharmacologically acceptable acid addition salt, L-Leu-L-Arg-L-Pro or its pharmacologically acceptable acid addition salt, and L-Ile-L-Arg-L-Ala-L-Gln-L-Gln or its pharmacologically acceptable acid addition salt, and a tripeptide represented by the formula L-(or D-) Leu-L-$X_{aa}$-L-Pro wherein $X_{aa}$ is Gly, Ala, Val, Ile, Thr, Asp, Glu, Lys, Orn, Cys, Met, Phe, Tyr, Trp, His or a hydroxyproline residue or a pharmacologically acceptable acid addition salt of the tripeptide wherein $X_{aa}$ is Lys, Orn, His or Arg, and a pharmacologically acceptable alkali or alkaline earth metal salt, ammonium salt or organic base salt of the tripeptide wherein $X_{aa}$ is Asp or Glu, and is in an amount effective to inhibit the angiotensin coverting enzyme.

11. The method of claim 10 wherein said at least one member is selected from the group consisting of L-Tyr-L-Val, L-Phe-L-Tyr, L-Val-L-Ala-L-Ala, L-Val-L-Ala-L-Ala, L-Val-L-Ser-L-Pro, L-Leu-L-Asn-L-Pro, L-Leu-L-Ala-L-Ala, L-Leu-L-Gln-L-Pro, L-Leu-L-Ser-L-Pro, L-Leu-L-Leu-L-Pro, L-Val-L-Ala-L-Tyr, L-Leu-L-Ala-L-Tyr, L-Ile-L-Arg-L-Ala or its pharmacologically acceptable acid addition salt, L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, L-Leu-L-Thr-L-Pro, L-Leu-L-Glu-L-Pro or its pharmacologically acceptable alkali or alkaline earth metal salt, ammonium salt or organic base salt, L-Leu-L-Tyr-L-Pro, and D-Leu-L-Arg-L-Pro or its pharmacologically acceptable acid addition salt.

12. The method of claim 10 wherein said at least one member is selected from the group consisting of L-Leu-L-Gln-L-Pro, L-Leu-L-Ser-L-Pro, L-Leu-L-Ala-L-Tyr, L-Ile-L-Arg-L-Ala or its pharmacologically acceptable acid addition salt, L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, and L-Leu-L-Thr-L-Pro.

13. A method for treatment or prophylaxis of hypertension of a human being or another mammal which comprises administering to the human being or another mammal a hypotensively effective amount of at least one member selected from the group consisting of L-Tyr-L-Val, L-Leu-L-Tyr, L-Leu-L-Phe, L-Phe-L-Tyr, L-Tyr-L-Arg or its pharmacologically acceptable acid addition salt, L-Leu-L-Ser-L-Pro, L-Leu-L-Gln-L-Pro, L-Val-L-Ser-L-Pro, L-Leu-L-Leu-L-Pro, L-Leu-L-Asn-L-Pro, L-Phe-L-Leu-L-Pro, L-Leu-L-Ala-L-Ala, L-Val-L-Ala-L-Ala, L-Leu-L-Gln-L-Gln, L-Val-L-Ala-L-Tyr, L-Leu-L-Ala-L-Tyr, L-Leu-L-Ser-L-His or its pharmacologically acceptable acid addition salt, L-Ile-L-Arg-L-Ala or its pharmacologically acceptable acid addition salt, L-Leu-L-Arg-L-Pro or its pharmacologically acceptable acid addition salt, and L-Ile-L-Arg-L-Ala-L-Gln-L-Gln or its pharmacologically acceptable acid addition salt, and a tripeptide represented by the formula L-(or D-) Leu-L-X$_{aa}$-L-Pro wherein X$_{aa}$ is Gly, Ala, Val, Ile, Thr, Asp, Glu, Lys, Orn, Cys, Met, Phe, Tyr, Trp, His or a hydroxyproline residue or a pharmacologically acceptable acid addition salt of the tripeptide wherein X$_{aa}$ is Lys, Orn, His or Arg, or a pharmacologically acceptable alkali or alkaline earth metal salt, ammonium salt or organic base salt of the tripeptide wherein X$_{aa}$ is Asp or Glu.

14. The method of claim 13 wherein said at least one member is selected from the group consisting of L-Tyr-L-Val, L-Phe-L-Tyr, L-Val-L-Ala-L-Ala, L-Val-L-Ala-L-Ala, L-Val-L-Ser-L-Pro, L-Leu-L-Asn-L-Pro, L-Leu-L-Ala-L-Ala, L-Leu-L-Gln-L-Pro, L-Leu-L-Ser-L-Pro, L-Leu-Leu-Pro, L-Val-L-Ala-L-Tyr, L-Leu-Ala-L-Tyr, L-Ile-L-Arg-L-Ala or its pharmacologically acceptable acid addition salt, L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, L-Leu-L-Thr-L-Pro, L-Leu-L-Glu-L-Pro or its pharmacologically acceptable alkali or alkaline earth metal salt, ammonium salt or organic base salt, L-Leu-L-Tyr-L-Pro, and D-Leu-L-Arg-L-Pro or its pharmacologically acceptable acid addition salt.

15. The method of claim 13 wherein said at least one member is selected from the group consisting of L-Leu-L-Gln-L-Pro, L-Leu-L-Ser-L-Pro, L-Leu-L-Ala-L-Tyr, L-Ile-L-Arg-L-Ala or its pharmacologically acceptable acid addition salt, L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, and L-Leu-L-Thr-L-Pro.

16. A compound selected from the group consisting of L-Val-L-Ala-L-Ala, L-Val-L-Ser-L-Pro, L-Leu-L-Asn-L-Pro, L-Leu-L-Ala-L-Ala, L-Leu-L-Gln-L-Pro, L-Leu-L-Ser-L-Pro, L-Leu-L-Leu-L-Pro, L-Val-L-Ala-L-Tyr, L-Leu-L-Ala-L-Tyr, L-Ile-L-Arg-L-Ala or its pharmacologically acceptable acid addition salt, L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, L-Leu-L-Thr-L-Pro, L-Leu-L-Gly-L-Pro, L-Leu-L-Tyr-L-Pro, and L-Leu-L-His-L-Pro or its pharmacologically acceptable acid addition salt.

17. The compound of claim 16 which is selected from the group consisting of L-Leu-L-Gln-L-Pro, L-Leu-L-Ser-L-Pro, L-Leu-L-Ala-L-Tyr, L-Ile-L-Arg-L-Ala or its pharmacologically acceptable acid addition salt, L-Leu-L-Arg-L-Pro or its pharmacologically acceptable acid addition salt, L-Leu-L-Lys-L-Pro and pharmacologically acceptable acid addition salt, L-Leu-L-Ala-L-Pro, and L-Leu-L-Thr-L-Pro.

18. An angiotensin converting enzyme inhibitor which either comprises at least one member which is selected from the group consisting of L-Val-L-Ala-L-Ala, L-Val-L-Ser-L-Pro, L-Leu-L-Asn-L-Pro, L-Leu-L-Ala-L-Ala, L-Leu-L-Gln-L-Pro, L-Leu-L-Ser-L-Pro, L-Leu-L-Leu-L-Pro, L-Val-L-Ala-L-Tyr, L-Leu-L-Ala-L-Tyr, L-Ile-L-Arg-L-Ala or its pharmacologically acceptable acid addition salt, L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, L-Leu-L-Thr-L-Pro, L-Leu-L-Gly-L-Pro, L-Leu-L-Tyr-L-Pro, and L-Leu-L-His-L-Pro or its pharmacologically acceptable acid addition salt, and is in an amount effective to inhibit the angiotensin converting enzyme of a human being or another mammal, and pharmaceutically acceptable carrier(s).

19. The angiotensin converting enzyme inhibitor of claim 18 wherein said at least one member is selected from the group consisting of L-Leu-L-Gln-L-Pro, L-Leu-L-Ser-L-Pro, L-Leu-L-Ala-L-Tyr, L-Ile-L-Arg-L-Ala or its pharmacologically acceptable acid addition salt, L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, and L-Leu-L-Thr-L-Pro.

20. A hypotensive pharmaceutical composition for human being or another mammal which either comprises a hypotensively effective amount of at least one member selected from the group consisting of L-Val-L-Ala-L-Ala, L-Val-L-Ser-L-Pro, L-Leu-L-Asn-L-Pro, L-Leu-L-Ala-L-Ala, L-Leu-L-Gln-L-Pro, L-Leu-L-Ser-L-Pro, L-Leu-L-Leu-L-Pro, L-Val-L-Ala-L-Tyr, L-Leu-L-Ala-L-Tyr, L-Ile-L-Arg-L-Ala or its pharmacologically acceptable acid addition salt, and L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, L-Leu-L-Thr-L-Pro, L-Leu-Gly-L-Pro, L-Leu-L-Tyr-L-Pro, and L-Leu-L-His-L-Pro or its pharmacologically acceptable acid addition salt, and pharmaceutically acceptable carrier(s).

21. The composition of claim 20 wherein said at least one member is selected from the group consisting of L-Leu-L-Gln-L-Pro, L-Leu-L-Ser-L-Pro, L-Leu-L-Ala-L-Tyr, L-Ile-L-Arg-L-Ala or its pharmacologically acceptable acid addition salt, and L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, and L-Leu-L-Thr-L-Pro.

22. A method for inhibition of the angiotensin converting enzyme in the body of a human being or another mammal which comprises administering to the human being or another mammal at least one member which is selected from the group consisting of L-Val-L-Ala-L-Ala, L-Val-L-Ser-L-Pro, L-Leu-L-Asn-L-Pro, and L-Leu-L-Ala-L-Ala, L-Leu-L-Gln-L-Pro, L-Leu-L-Ser-L-Pro, L-Leu-L-Leu-L-Pro, L-Val-L-Ala-L-Tyr, L-Leu-L-Ala-L-Tyr, L-Ile-L-Arg-L-Ala or its pharmacologically acceptable acid addition salt, L-Leu-L-Arg-L-Pro or its pharmacologically acceptable acid addition salt, L-Leu-L-Lys-L-Pro or its pharmacologically acceptable acid addition salt, L-Leu-L-Ala-L-Pro, L-Leu-L-Thr-L-Pro, L-Gly-L-Pro, L-Leu-L-Tyr-L-Pro, and L-Leu-L-His-L-Pro or its pharmacologically acceptable acid addition salt, and is in an amount effective to inhibit the angiotensin converting enzyme.

23. The method of claim 22 wherein said at least one member is selected from the group consisting of L-Leu-L-Gln-L-Pro, L-Leu-L-Ser-L-Pro, L-Leu-L-Ala-L-Tyr, L-Ile-L-Arg-L-Ala or its pharmacologically acceptable acid addition salt, L-Leu-L-Arg-L-Pro or its pharmacologically acid addition salt, L-Leu-L-Lys-L-Pro or its pharmacologically acid addition salt, L-Leu-L-Ala-L-Pro, and L-Leu-L-Thr-L-Pro.

24. A method for treatment or prophylaxis of hypertension of a human being or another mammal which comprises administering to the human being or another mammal a hypotensively effective amount of at least one member selected from the group consisting of L-Val-L-Ala-L-Ala, L-Val-L-Ser-L-Pro, L-Leu-L-Asn-L-Pro, L-Leu-L-Ala-L-Ala, L-Leu-L-Gln-L-Pro, L-Leu-L-Ser-L-Pro, L-Leu-L-Leu-L-Pro, L-Val-L-Ala-L-Tyr, L-Leu-L-Ala-L-Tyr, L-Ile-L-Arg-L-Ala or its pharmacologically acid addition salt, L-Leu-L-Arg-L-Pro or its pharmacologically acid addition salt, L-Leu-L-Lys-L-Pro or its pharmacologically acid addition salt, L-Leu-L-Ala-L-Pro, L-Leu-L-Thr-L-Pro, L-Leu-L-Gly-L-Pro, L-Leu-L-Tyr-L-Pro, and L-Leu-L-His-L-Pro or its pharmacologically acid addition salt.

25. The method of claim 24 wherein said at least one member is selected from the group consisting of L-Leu-L-Gln-L-Pro, L-Leu-L-Ser-L-Pro, L-Leu-L-Ala-L-Tyr, L-Ile-L-Arg-L-Ala or its pharmacologically acid addition salt, and L-Leu-L-Arg-L-Pro or its pharmacologically acid addition salt, L-Leu-L-Lys-L-Pro or its pharmacologically acid addition salt, L-Leu-L-Ala-L-Pro and L-Leu-L-Thr-L-Pro.

26. The hypotensive pharmaceutical composition of claim 20 in the form of a food.

* * * * *